US 6,596,896 B2
Jul. 22, 2003

(54) PROCESS FOR PRODUCING AROMATIC CARBONATE (75) Inventors: Eishin Yoshisato, Iwakuni (JP); Tetsuo Ban, Iwakuni (JP); Masaharu Muramoto, Iwakuni (JP); Yuzo Fujiwara, Fukuoka (JP); Teizo Yamaji, Fukuoka (JP); Chengguo Jia, Fukuoka (JP); Guochuan Yin, Fukuoka (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/220,597
(22) PCT Filed: Mar. 1, 2001
(86) PCT No.: PCT/JP01/01565
§ 371 (c)(1), (2), (4) Date: Sep. 3, 2002
(87) PCT Pub. No.: WO01/64616
PCT Pub. Date: Sep. 7, 2001

(65) Prior Publication Data
US 2003/0032831 A1 Feb. 13, 2003

(30) Foreign Application Priority Data

Mar. 3, 2000 (JP) ........................................ 2000-058591
Aug. 16, 2000 (JP) ........................................ 2000-246725
Sep. 21, 2000 (JP) ........................................ 2000-286779

(51) Int. Cl.[7] ............................................. C07C 69/96
(52) U.S. Cl. ........................................ 558/274; 502/311
(58) Field of Search ......................... 558/274; 502/311

(56) References Cited

U.S. PATENT DOCUMENTS 5,821,377 A  10/1998 Buysch et al.
6,534,670 B2 * 3/2003 Yoshisato ............... 558/274

FOREIGN PATENT DOCUMENTS

| JP | 56-38144 B2 | 9/1981 |
| JP | 60-75447 | 4/1985 |
| JP | 60-075447 A | 4/1985 |
| JP | 02-104564 A | 4/1990 |
| JP | 08-092168 A | 4/1996 |
| JP | 08-099935 A | 4/1996 |
| JP | 08-281114 A | 10/1996 |
| JP | 09-241372 A | 9/1997 |
| JP | 9-241372 | 9/1997 |

OTHER PUBLICATIONS

Goyal, et al, "Effect of inorganic redox cocatalyst of Pd–catalyzed oxidative carbonylation of phenol for direct synthesis of diphenyl carbonate," *Catalysis Letters*, 54 (1998), p. 29–31.

(List continued on next page.)

*Primary Examiner*—Joseph K. McKane
*Assistant Examiner*—Robert Shiao
(74) *Attorney, Agent, or Firm*—Sughrue Mion, PLLC

(57) ABSTRACT

A process for producing an aromatic carbonate by reacting an aromatic monohydroxy compound with carbon monoxide and molecular oxygen, wherein the reaction is carried out in the presence of:
(a) palladium or a palladium compound (component (a));
(b) a redox catalyst (component (b));
(c) a heteropoly-acid or salt thereof (component (c)); and
(d) a quaternary ammonium salt or quaternary phosphonium salt (component (d)),
and under dehydration conditions.

According to the present invention, an aromatic carbonate can be produced from an aromatic monohydroxy compound by a simple process economically and efficiently.

15 Claims, 1 Drawing Sheet

OTHER PUBLICATIONS

Baker, et al, "Present General Status of Understanding of Heteropoly Electrolytes and a Tracing of Some Major Highlights in the History of Their Elucidation," *Chem. Rev.,* 1998, 98, pp. 3–49.

*Inorganic Syntheses,* vol. 27, Alvin P. Ginsburg, Editor–in–Chief, John Wiley & Sons Publishers, p. 95.

Patent Abstracts of Japan, JP 60–075447, dated Apr. 27, 1985.

Patent Abstracts of Japan, JP 02–104564, dated Apr. 17, 1990.

Patent Abstracts of Japan, JP 08–092168, dated Apr. 9, 1996.

Patent Abstracts of Japan, JP 08–099935, dated Apr. 16, 1996.

Patent Abstracts of Japan, JP 08–281114, dated Oct. 29, 1996.

Patent Abstracts of Japan, JP 09–241372, dated Sep. 16, 1997.

Derwent WPI Abstract, JP56–38144, dated Sep. 4, 1981.

* cited by examiner

F I G. 1

PROCESS FOR PRODUCING AROMATIC CARBONATE

FIELD OF THE INVENTION

The present invention relates to an aromatic carbonate production process. More specifically, it relates to a process for producing an aromatic carbonate by reacting an aromatic monohydroxy compound with carbon monoxide and molecular oxygen in the presence of a specific catalyst.

PRIOR ART

Aromatic carbonates typified by diphenyl carbonate are very useful compounds as a raw material for polycarbonates. Heretofore, the aromatic carbonates have been produced by reacting an aromatic monohydroxy compound with phosgene. However, this process involves many problems to be solved as an industrial production process because phosgene has high toxicity and a large amount of an inorganic salt is by-produced. Then, some processes for producing an aromatic carbonate without using phosgene are proposed. That is, the following processes are proposed to produce an aromatic carbonate by reacting an aromatic monohydroxy compound with carbon monoxide and molecular oxygen. For example, JP-B 56-38144 (the term "JP-B" as used, herein means an "examined Japanese patent publication") discloses a process in which a phenol is reacted with carbon monoxide in the presence of a compound containing the group IIIA, IVA, VA, VIA, IB, IIB, IVB, VB, VIB, VIIB or VIIIB metal of the periodic table, a base and a palladium catalyst, JP-A 2-104564 (the term "JP-A" as used herein means an "unexamined published Japanese patent application") discloses a process which uses a palladium compound, manganese compound, tetraalkylammonium salt and quinone, JP-A 8-92168 teaches a process which uses a palladium compound, alkali metal halide and activated carbon, JP-A 8-99935 teaches a process which uses a palladium compound, lead compound, quaternary ammonium halide and copper compound, and JP-A 8-281114 proposes a process in which a reaction is carried out in the presence of a supporting catalyst containing a platinum group metal compound and a metal compound which serves as a co-catalyst carried on a known carrier, a quaternary ammonium or phosphonium salt and a base.

Further, Catalysis Letters 54 (1998) reports at pp. 29–31 that $Ce(OAc)_3 \cdot H_2O$ provides a high aromatic carbonate production yield of 76% out of inorganic redox co-catalysts in a process for carrying out a reaction in the presence of a catalytic system consisting of a palladium catalyst, organic redox co-catalyst, base and desiccant.

As described above, the catalytic system of the prior art for producing an aromatic carbonate by reacting an aromatic hydroxyl compound with carbon monoxide and molecular oxygen consists of a platinum group compound such as an expensive palladium compound, an inorganic redox agent such as a manganese, cobalt or cerium metal compound and a co-catalyst such as a quaternary ammonium salt as essential components, and an expensive base and ligand or additives such as hydroquinone and quinone are used. Since the reaction system is complicated, it is difficult to separate an aromatic carbonate which is the reaction product from catalytic components and to purify it due to insufficient reaction selectivity. In addition, the yield is insufficient, the total pressure is relatively high to improve the rate of reaction, and an explosive mixed gas may be formed through operation. Therefore, much attention must be paid to the composition of the obtained product, thereby posing a safety problem.

Since an expensive precious metal such as palladium, a redox agent and a relatively large amount of a quaternary ammonium salt are used in the above process, not only the activity and selectivity of the catalytic system but also the recyclability of the catalytic system are extremely important factors to carry out the process industrially and economically. For this purpose, an attempt has been made to make heterogeneous a part or most part of a palladium catalyst by carrying palladium on a heterogeneous carrier such as activated carbon so as to improve recyclability (JP-A8-92168). According to researches conducted by the present inventors, the catalyst strongly adsorbs part of the reaction product, thereby impairing the persistence of the reaction. Therefore, it has been found that the regeneration of the catalyst is complicated and it is not preferred to use the regenerated catalyst in an industrial process. The above JP-A 8-281114 proposes a process in which a metal oxide containing a metal oxide having functions as a redox agent is used as a carrier or part of a carrier. However, researches conducted by the present inventor have revealed that the catalyst is unsatisfactory in terms of reaction yield and selectivity, the carrying power of a precious metal compound such as a palladium compound may be insufficient and the palladium metal and the redox agent dissolve in a reaction solution. As a result, it has been found that this process is not preferred as an economical process.

Thus, a catalytic system which makes it possible to produce an aromatic carbonate simply and efficiently by reacting an aromatic hydroxy compound with carbon monoxide and molecular oxygen has not been found yet.

SUMMARY OF THE INVENTION

It is an object of the present invention to provide a catalytic system which shows high activity and selectivity so that an aromatic carbonate can be produced economically and efficiently by reacting an aromatic monohydroxy compound with carbon monoxide and molecular oxygen and a process for producing an aromatic carbonate in the presence of the above catalytic system. Problems to be solved by the Invention The present inventor has conducted intensive studies to find a catalytic system having the above function and has discovered that an aromatic carbonate can be obtained efficiently and industrially advantageously when an aromatic monohydroxy compound is reacted with carbon monoxide and molecular oxygen in the present of a specific catalytic system. Thus, the present invention has been accomplished based on this discovery.

According to the present invention, there is provided a process for producing an aromatic carbonate by reacting an aromatic monohydroxy compound with carbon monoxide and molecular oxygen, wherein the reaction is carried out under dehydration condition and in the presence of catalysts consisting of (a) palladium or a palladium compound (component (a)), (b) a redox catalyst (component (b)), (c) a heteropoly-acid or salt thereof (component (c)) and (d) a quaternary ammonium salt or quaternary phosphonium salt (component (d)).

DETAILED DESCRIPTION OF THE PREFERRED EMBODIMENT

Illustrative examples of the aromatic monohydroxy compound which can be used in the reaction of the present invention include phenol, cresol, xylenol, substituted phenols such as trimethylphenol, tetramethylphenol, ethylphenol, propylphenol, methoxyphenol, ethoxyphenol, chlorophenol and bromophenol, isomers thereof, naphthol and substituted naphthols such as methylnaphthol, chloronaphthol and bromonaphthol, and isomers thereof. Out of these, phenol is particularly preferred.

Carbon monoxide and molecular oxygen which are gas components used in the reaction of the present invention may be used in a diluted state with another gas which does not exert a bad influence upon the reaction, such as nitrogen, argon or carbon dioxide. Air may be used as the molecular oxygen.

The catalytic system used in the reaction of the present invention comprises at least the following components (a), (b), (c) and (d):

(a) palladium or a palladium compound (component (a)), (b) a redox catalyst (component (b)), (c) a heteropoly-acid or salt thereof (component (c)), and (d) a quaternary ammonium salt or quaternary phosphonium salt (component (d)).

In the above catalytic system of the present invention, the component (a) is metallic palladium or a palladium compound. Examples of the component (a) include carried metallic palladium such as palladium black, palladium-on-carbon, palladium-on-alumina and palladium-on-silica; inorganic salts of palladium such as palladium chloride, palladium bromide, palladium iodide, palladium sulfate and palladium nitrate; organic salts of palladium such as palladium acetate, palladium oxalate and palladium benzoate; chelate coordinated palladium complex compounds such as palladium acetyl acetonate and piperidyl palladium; and complex compounds such as [Pd(CO)Cl], $PdCl_2(PhCN)_2$, $PdCl_2(PPh_3)_2$, $PdCO(PPh_3)_3$, $[Pd(NH_3)_4]Cl_2$, $[Pd(en)_2]Cl_2$ (en=ethylenediamine) and $Pd(C_2H_4)(PPh_3)_2$. They may be formed in a reaction system. "Ph" in the chemical formulas of the above palladium complex compounds represents a phenyl group. These palladium and palladium compounds may be used alone or in combination of two or more.

The amount of palladium used as the component (a) is preferably in the range of 1 to $10^{-6}$ mol, particularly preferably $10^{-2}$ to $10^{-5}$ mol in terms of palladium atom based on 1 mol of the aromatic monohydroxy compound.

Examples of the redox agent as the component (b) include compounds of the IIIA, IVA, VA, VIA, IB, IIB, VIB, VIIB and iron (VIII) groups and rare earth metals (IIIB) of the periodic table. These metal compounds may be used in the form of various compounds, for example, complex salts such as halides, oxides, hydroxides, carbonates, organic carbonates, diketone salts, oxalates or salicylates, and complexes coordinated with carbon monoxide, olefins, amines and phosphines. The metal compound preferred as the redox agent is a compound of at least one metal selected from the group consisting of manganese, cobalt, copper, cerium and lead, out of which manganese or cerium is particularly preferred, and out of which manganese is the most preferred. The amount of the redox agent is not particularly limited but is preferably 0.1 to 1,000 mols, particularly preferably 0.1 to 100 mols based on 1 mol of the carbon palladium or palladium compound.

The component (c) used in the catalytic system of the present invention is a heteropoly-acid or salt thereof.

The heteropoly-acid is a polyacid obtained by the dehydration and condensation of two or more oxyacids (oxoacids) and consists of a cluster of oxide molecules (polyanion) having negative charge and protons (refer to Chemical Reviews, vol. 98, pp. 3–49, 1998). It is preferably a heteropoly-acid having a structure called "Kegin" whose anion is represented by the following general formula (1):

$$XM_{12}O_{40} \tag{1}$$

wherein X is P, Si, As or Ge, and M is Mo or W, with the proviso that some of M's may be substituted by V, Mn, Co, Cu, Fe or Zn.

What has protons for this anion is called "polyacids" but a salt obtained by substituting the proton by cations is also effective in the present invention. The cation is an alkali metal ion such as Li, Na, K, Rb or Cs; alkali earth metal ion such as Ca or Mg; metal ion such as Cu, Zn or Al; transition metal ion such as Fe, Co, Ni, Mn or Cr; or rare earth metal ion such as Ce or La. Further, a salt soluble in an organic solvent such as an ammonium salt or organic ammonium salt may be used. Since the solubility of the heteropoly-acid salt differs according to the type of a salt, the heteropoly-acid may be used as a homogeneous reaction catalyst or a heterogeneous reaction catalyst.

Out of the above heteropoly-acids having a Kegin structure, the particularly preferred as component (c) in the present invention is a heteropoly-acid having a Kegin structure whose anion is represented by the following structural formula (2) or a salt thereof:

$$X(MO)_n(W)_m(V)_pO_{40} \tag{2}$$

wherein X is elemental P or Si, and n, m and p are each an integer of 0 to 12, with the proviso that n+m+p=12.

Examples of the anion of the heteropoly-acid of the above formula (2) include molybdenumphosphoric acids ($PMo_{12}O_{40}$), tungstophosphoric acids ($PW_{12}O_{40}$), molybdenumsilicic acids ($SiMo_{12}O_{40}$), tungstosilicic acids ($SiW_{12}O_{40}$), tungstomolybdenumphosphoric acids (such as $PMoW_{11}O_{40}$, $PMo_3W_9O_{40}$, $PMo_5W_7O_{40}$, $PMo_7W_5O_{40}$, $PMo_9W_3O_{40}$, $PMo_{11}WO_{40}$, $PMo_2W_{10}O_{40}$, $PMo_4W_8O_{40}$, $PMo_6W_6O_{40}$, $PMo_8W_4O_{40}$ and $PMo_{10}W_2O_{40}$), vanadomolybdenumphosphoric acids (such as $PMo_{11}V_1O_{40}$, $PMo_{10}V_2O_{40}$, $PMo_9V_3O_{40}$, $PMo_4V_8O_{40}$ and $PMo_{10}V_2O_{40}$, vanadotungstenphosphoric acids (such as $PW_9V_3O_{40}$, $PW_{10}V_2O_{40}$ and $PW_{11}V_1O_{40}$), molybdotungstensilicic acids (such as $SiMoW_{11}O_{40}$, $SiMo_2W_{10}O_{40}$, $SiMo_4W_8O_{40}$, $SiMo_5W_7O_{40}$, $SiMo_7W_5O_{40}$, $SiMo_9W_3O_{40}$, $SiMo_{10}W_2O_{40}$, $SiMo_{11}WO_{40}$, $SiMo_3W_9O_{40}$, $SiMo_6W_6O_{40}$, and $SiMo_8W_4O_{40}$), vanadotungstensilicic acids (such as $SiW_{11}V_1O_{40}$, $SiW_{10}V_2O_{40}$, $SiW_9V_3O_{40}$, $SiW_8V_4O_{40}$, $SiW_6V_6O_{40}$ and $SiW_8V_4O_{40}$, and vanadomolybden acids (such as $SiMo_{11}V_1O_{40}$, $SiMo_{10}V_2O_{40}$, $SiMo_9V_3O_{40}$, $SiMo_8V_4O_{40}$, $SiMo_6V_6O_{40}$ and $SiMo_8V_4O_{40}$). These heteropoly-acids may be used alone or in admixture of two or more. A cation salt of a heteropoly-acid or a mixture thereof may also be used as described above.

The heteropoly-acid as the component (c) may be a quaternary ammonium salt or quaternary phosphonium salt of a heteropoly-acid. By using one of the above salts, the corrosion of a reactor by the strong acidity of the heteropoly-acid can be suppressed. In addition, the above salt is advantageously used as a homogeneous reaction catalyst because it has high solubility in a reaction mixture or organic solvent.

The quaternary ammonium ion and quaternary phosphonium ion forming a salt with a heteropoly-acid are represented by the formulas $R_1R_2R_3R_4N^+$ and $R_1R_2R_3R_4P^+$, respectively ($R_1$ to $R_4$ are each an alkyl group having 1 to 8 carbon atoms or aryl group having 6 to 12 carbon atoms and may be the same or different).

Illustrative examples of the quaternary ammonium ion and the quaternary phosphonium ion include tetramethylammonium ion, tetraethylammonium ion, tetra-n-butylammonium ion, 1-n-hexadecylpyridinium ion, tetrabutylammonium ion, phenyltrimethylammonium ion, benzyltrimethylammonium ion, tetramethylphosphonium ion, tetraethylphosphonium ion, tetrabutylphosphonium ion, hexadecyltributylphosphonium ion and tetraphenylphosphonium ion. A heteropoly-acid salt obtained by substituting some or all of protons of the heteropoly-acid may also be used. These heteropoly-acid salts may be used in a homogeneous reaction catalyst and a homogeneous reaction catalyst as the solubility of each of the heteropoly-acid salts differs according to the type of a salt.

The quaternary ammonium salt or quaternary phosphonium salt of a heteropoly-acid can be easily prepared by the following methods. The most simple and effective method is that an aqueous solution of the above heteropoly-acid and an aqueous solution of a quaternary ammonium or quaternary phosphonium halogen salt or mineral acid salt are mixed together and the quaternary ammonium salt or quaternary phosphonium salt of the heteropoly-acid formed as a precipitate is separated by filtration. Strong acidic protons which cause corrosion can be easily removed because they are liberated as a water-soluble hydrogen halide or mineral acid.

Another method is that the quaternary ammonium salt or quaternary phosphonium salt of a heteropoly-acid is prepared by carrying out a metathesis reaction (cation exchange reaction) between an aqueous solution of an alkali salt such as a sodium salt or potassium salt of a heteropoly-acid and an aqueous solution of a halogen salt or mineral acid salt of quaternary ammonium or quaternary phosphonium. Still another method is that a quaternary ammonium salt or phosphonium salt of interest is directly obtained by the preparation of a heteropoly-acid (refer to Inorg. Syn., vol. 27, pp. 95).

The above heteropoly-acid as the component (c) in the catalytic system of the present invention may be a composite of a transition metal element and a heteropoly-acid. It can be said that this composite is a compound containing a transition metal element which is ionically or coordinately bonded to a heteropoly-acid. The transition metal element forming this composite is selected from the transition metal elements of the groups III to XII of the fourth to sixth periods of the periodic table. It is preferably Co, Cu or Ce. A composite containing one of the above transition metal elements substituted for the proton or cation of a heteropoly-acid is generally used because it is relatively easily prepared and has stability. According to circumstances, a composite containing one of the above transition metal elements substituted for Mo or W forming the anion of a heteropoly-acid may also be used.

The composite of a heteropoly-acid and a transition metal element may be prepared by the following methods. An example of it includes a composite containing a transition metal element introduced into the site of a cation for the above heteropolyanion alone or together with a proton or another cation. The composite of a transition metal element and a heteropoly-acid can be obtained by a direct reaction between a transition metal element salt and a heteropoly-acid or salt thereof. The most simple and effective method is that a heteropoly-acid and cerium acetate $(Ce(OAc)_3)$ are reacted with each other to liberate and remove acetic acid. With this method, a composite of cerium and a heteropoly-acid in which metallic cerium has been introduced into the site of the cation of the heteropoly-acid in the form of a tervalent ion and an excessive cation remains as a proton can be obtained and further a composite of cerium and a heteropoly-acid in which the remaining proton has been substituted by another cation may also be obtained. Alternatively, the composite in which the transition metal has been introduced into the site of the cation of the heteropoly-acid can be obtained by making use of a so-called metathesis reaction between an alkali metal salt or alkali earth metal salt of the heteropoly-acid and a transition metal salt. For example, a barium salt of a heteropoly-acid is prepared by reacting the heteropoly-acid with barium carbonate and then reacted with cerium sulfate to obtain a composite containing cerium introduced into the site of the cation of the heteropoly-acid. Still another method is that a heteropoly-acid is neutralized with a base such as potassium hydrogen carbonate to activate the bonding of the anion of the heteropoly-acid and then a transition metal salt is caused to act thereon to introduce a transition metal into the heteropoly-acid.

The above composites of transition metals and heteropoly-acids may be used alone or in admixture of two or more, or may be carried on an appropriate carrier as the component (c). The carrier is selected from alumina, silica gel, silica alumna, magnesia, titanium oxide, zirconium oxide, cerium oxide and mixtures thereof.

The amount of the component (c) is 0.1 to 200 mols, preferably 0.1 to 100 mols based on 1 mol of the metallic palladium or palladium compound (component (a)).

The component (d) used in the catalytic system of the present invention is a quaternary ammonium salt or quaternary phosphonium salt represented by the formulas $R_1R_2R_3R_4NX$ or $R_1R_2R_3R_4PX$ ($R_1$ to $R_4$ are the same or different and each an alkyl group having 1 to 8 carbon atoms or aryl group having 6 to 12 carbon atoms, X is an anion such as hydroxyl group, alkoxy group, phenoxy group or halide such as chloride, bromide or iodide), respectively. Out of these, tetra-n-butylammonium salts and tetraphenyl phosphonium salts are preferred. The amount of the quaternary ammonium salt or quaternary phosphonium salt used in a reaction is 0.1 to 1,000 mols, particularly preferably 1 to 100 mols based on 1 mol of the metallic palladium or palladium compound (component (a)).

The catalytic system in the reaction of the present invention comprises at least four components (a), (b), (c) and (d) described above and these four components may be used as independent compounds (or salts or composites). However, the component (a) and the component (c) may be used as a composite of the two components. That is, a composite of palladium and a heteropoly-acid may be prepared and used. In this case, the components (a) and (c) are used as a single compound.

It can be said that this composite of palladium and a heteropoly-acid is a compound containing palladium ionically or coordinately bonded to the heteropoly-acid. Stated more specifically, a composite in which the proton or cation of the heteropoly-acid has been substituted by palladium is generally used because it is relatively easily prepared and has stability. According to circumstances, a composite containing palladium substituted for Mo or W forming the anion of the heteropoly-acid may also be used.

Examples of the composite of a heteropoly-acid and palladium are given below and may be prepared by the following methods. An example of it includes a composite containing palladium introduced into the site of a cation for the above heteropolyanion alone or together with a proton or another cation. The composite of palladium and a heteropoly-acid can be obtained by a direct reaction between a palladium salt and a heteropoly-acid or salt thereof. The most simple and effective method is that a heteropoly-acid and palladium acetate (Pd(OAc)$_2$) are reacted with each other to liberate and remove acetic acid. With this method, a composite of palladium and a heteropoly-acid in which metallic palladium has been introduced into the site of the cation of the heteropoly-acid in the form of a divalent ion and an excessive cation remains as a proton can be obtained and further a composite of palladium and a heteropoly-acid in which the remaining proton has been substituted by another cation may also be obtained. Alternatively, the composite in which palladium has been introduced into the site of the cation of the heteropoly-acid can be obtained by making use of a so-called metathesis reaction between an alkali metal salt or alkali earth metal salt of the heteropoly-acid and a palladium metal salt. For example, a barium salt of a heteropoly-acid is prepared by reacting the heteropoly-acid with barium carbonate and then reacted with palladium sulfate to obtain a composite containing palladium introduced into the site of the cation of the heteropoly-acid. Still another method is that a heteropoly-acid is neutralized with a base such as potassium hydrogen carbonate to activate the bonding of the anion of the heteropoly-acid and then a palladium salt is caused to act thereon to introduce palladium into the heteropoly-acid.

The above composites of palladium and heteropoly-acids may be used alone or in admixture of two or more, or may be carried on an appropriate carrier as the components (a) and (c). The carrier is selected from alumina, silica gel, silica alumna, magnesia, titanium oxide, zirconium oxide, cerium oxide and mixtures thereof. The heteropoly-acid and palladium are generally used in the composite in a molar ratio of 1:1. When the composite is used, the amounts of the component (a) and the component (c) should be selected from the above respective ranges in consideration of this.

As described above, the catalytic system in the reaction of the present invention comprises at least the components (a), (b), (c) and (d). Preferably, it further comprises a quinone or hydroquinone (component (e)). Examples of the quinone as the component (e) include 1,4-benzoquinone, 1,2-benzoquinone, 3,5-di-t-butyl-1,2-benzoquinone, 1,4-naphthoquione, anthraquinone, 2-ethyl-9,10-anthraquinone and 1,4-phenanthrenequinone and examples of the hydroquinone include hydroquinone, catechol, 3,5-di-t-butylcatechol, resorcin, 1,4-dihydronaphthalene, 9,10-dihydroanthracene, 2-ethyl-9,10-dihydroanthracene and 1,4-dihydroxyphenanthrene. The amount of quinone or hydroquinone is preferably 0.1 to 200 mols, more preferably 0.5 to 200 mols based on 1 mol of the metallic palladium or palladium compound (component (a)).

A reaction for forming an aromatic carbonate in the present invention is carried out by charging an aromatic monohydroxy compound and the above catalytic system into a reactor, supplying carbon monoxide and molecular oxygen under pressure, and heating.

To promote this reaction efficiently at this point, it is important that water formed by the reaction should be removed from a reaction system as swiftly and efficiently as possible. For this purpose, a dessicant such as a molecular sieve is existent in the reaction system. It is also effective to use a gas circulation reactor to eliminate formed water by circulating carbon monoxide and molecular oxygen from the reaction system continuously. Further, an organic solvent which boils with water can be used to eliminate water from the reaction system efficiently and continuously.

The organic solvent which boils with water and is used in the present invention is an organic solvent whose azeotropy is observed but an organic solvent which directly takes part in the reaction and reacts with raw materials or the reaction product is not appropriate even if it boils with water. Therefore, organic solvents having an active hydrogen such as aliphatic alcohols including ethanol and primary and secondary amines are not appropriate because they may take part in the reaction. Since azeotropic compositions are affected by not only the co-existent reaction product but also reaction temperature and pressure, the azeotropic temperature of the organic solvent with water under reaction pressure is desirably not much higher than the reaction temperature.

Since the reaction temperature of the present invention is 30 to 200° C., preferably 50 to 150° C., the azeotropic temperature under reaction pressure is preferably close to the above temperature range. Examples of the organic solvent which satisfies the above conditions include esters such as methyl acetate, ethyl acetate, ethyl acrylate, methyl methacrylate, methyl butyrate and ethyl benzoate; ethers such as diethyl ether, diisopropyl ether, methyl-t-butyl ether, 1,2-dimethoxyethane, tetrahydrofuran, anisole, 1,3-dioxane and 1,4-dioxane; ketones such as cyclohexanone, 3-heptanone, 4-heptanone and acetylacetone; halides such as chlorobenzene, chloroform and carbon tetrachloride; nitrogen-containing compounds such as nitroethane, acrylonitrile, pyridine, 2-methylpyridine, 3-methylpyridine and 4-methylpyridine; aliphatic hydrocarbons such as cyclohexane, hexane, octane and didecane; and aromatic hydrocarbons such as benzene, toluene, xylene and naphthalene. A mixture of two different organic solvents forming a three-component azeotrope with water may also be used. Such combinations of organic solvents are numerous, as exemplified by a combination of acetonitrile and benzene, a combination of methyl ethyl ketone and hexane, and a combination of nitromethane and octane. Out of these, organic solvents which do not have miscibility with water are particularly preferred in view of separation from water and recycling. Ethers such as methyl-t-butyl ether, 1,2-dimethoxyethane and tetrahydrofuran, and aromatic hydrocarbons such as benzene, toluene and xylene are particularly preferred from the viewpoints of small chemical reactivity, small influence upon the reaction system and separation between the catalyst components and the product.

The amount of the organic solvent forming an azeotrope with water at the time of reaction is 10 to 0.01 part by weight, preferably 5 to 0.02 part by weight based on 1 part by weight of the aromatic monohydroxy compound as a raw material. The above organic solvent which boils with water may be liquid, mixed with the aromatic monohydroxy compound as a raw material and then supplied into a reactor, or may be partially evaporated and supplied into a reactor together with gaseous raw materials. After the organic solvent which boils with water stays in the reactor, part or most of the solvent is discharged from the reactor as a gas together with reactive gases used excessively and co-boiling water. Thus, water is separated and removed from the discharged gaseous mixture and then the organic solvent and the reactive gases are returned to the reactor, thereby making it possible to eliminate formed water from the reactor continuously without losing the organic solvent and reactive gases (carbon monoxide and molecular oxygen) substantially.

The reaction of the present invention is preferably carried out by maintaining the partial pressure of carbon monoxide and the partial pressure of molecular oxygen contained in the mixed gas at constant levels and the total pressure at a constant level in the reaction system.

Although the partial pressures of carbon monoxide and molecular oxygen are preferably maintained at constant levels, the ratio of these materials is preferably outside the explosive range from the viewpoint of safety. The partial pressures of carbon monoxide and molecular oxygen which differ according to the total pressure and the proportion of an inert gas component contained therein is generally selected from a range of 5:1 to 30:1. The reaction can be carried out by maintaining the ratio of gases to be supplied during the reaction at a constant level, maintaining the optimum gas composition and continuously removing water formed by the reaction at the same time.

The reaction of the present invention can be carried out without restriction on the pressure. A too high pressure is not advantageous from the viewpoints of the structure and operation of the apparatus and safety. The total pressure is preferably 50 kg/cm$^2$·G or less, particularly preferably 30 kg/cm$^2$·G or less.

The reaction temperature is 30 to 200° C., preferably 50 to 150° C. The, reaction time which differs according to reaction conditions is generally several minutes to several hours.

Although various inert solvents may be used as the solvent for the reaction, solvents having a relatively high vapor pressure are gradually removed from the reactor together with reactive gases when the reaction is carried out under the circulation of the above gases. Therefore, the aromatic monohydroxy compound as a raw material is generally used as a reaction solvent and other solvent may not be particularly used.

EXPLANATIONS OF LETTERS OR NOTATIONS

| 1  | reactive gas          |
|----|-----------------------|
| 2  | reactive gas          |
| 3  | valve                 |
| 4  | valve                 |
| 5  | pressure regulator    |
| 6  | pressure regulator    |
| 7  | mass flow controller  |
| 8  | mass flow controller  |
| 9  | gas mixture preheater |
| 10 | reactor               |
| 11 | cold trap             |
| 12 | pressure regulator    |

Figure 1:
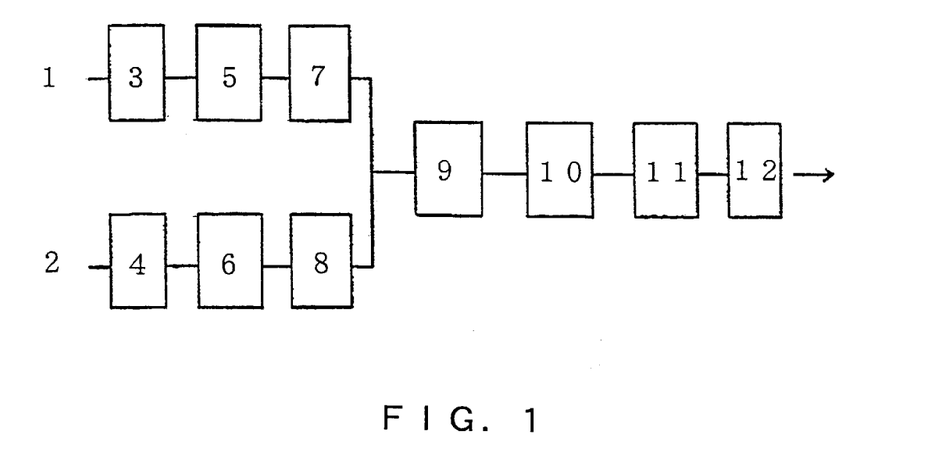
FIG. 1 is a schematic diagram showing a small-sized gas circulation reaction system for carrying out the present invention.

FIG. 1 is a schematic diagram showing a small-sized gas circulation reaction system for carrying out the present invention. The reaction system shown in FIG. 1 enables a mixed gas of carbon monoxide and oxygen (or air) whose molar ratio and partial pressures are maintained at constant levels to be continuously supplied at a constant flow rate of about 10 to 800 ml/min. The reactor 10 has a capacity of 100 ml and a diameter of 30 mm and is cylindrical and equipped with a gas blowing tube and rotary agitation elements. When the reactive gas 1 is carbon monoxide and the reactive gas 2 is molecular oxygen (or air), they pass through the valves 3 and 4 and are adjusted to pressures 1 to 5 atm higher than the pressure of the pressure regulator 12 for controlling a predetermined reaction pressure by the pressure regulators 5 and 6, respectively. Thereby, predetermined amounts of gases are supplied to the reactor 10 through the gas mixture preheater 9 from the mass flow controllers 7 and 8, respectively. The gas components passing through the reactor 10 go through the cold trap 11 and are discharged from the pressure regulator 12. The pressure of the reactor 10 is adjusted by the pressure regulator 12.

In the reaction method shown in FIG. 1, the gas coming from the reactor 10 is introduced into the cold trap 11 where part of formed water and the solvent are collected and unreacted gas is collected from the pressure regulator 12. The gas whose composition has been controlled as required can be recycled.

After the end of the reaction, the reaction mixture is taken out from the reactor and the catalyst of the present invention can be separated by filtration, centrifugal separation or magnetic separation, recovered and recycled. In the case of a fixed bed system, this separation operation is not necessary. The aromatic carbonate of interest may be separated and purified by filtration, distillation or crystallization to be isolated.

The following examples are given to further illustrate the process of the present invention.

In the following examples, a reaction was carried out in the reaction system shown in FIG. 1 unless otherwise stated.

EXAMPLE 1

Using the reaction system shown in FIG. 1, the inside of a reactor containing 47 g (0.50 mol) of phenol, 36.0 mg (0.16 mmol) of palladium acetate (Pd(OAc)$_2$), 136 mg (0.047 mmol) of tungstomolybdenumphosphoric acid (H$_3$PMo$_6$W$_6$O$_{40}$·30H$_2$O), 55 mg (0.32 mmol) of manganese acetate (Mn(OAc)$_2$), 968 mg (3 mmol) of tetra-n-butylammonium bromide (Bu$_4$NBr) and 7.0 g of a molecular sieve (powder having a particle diameter of 4 Å) was substituted with carbon monoxide. Right after the temperature of the reactor was raised to 80° C. and the pressure of the reactor was increased to 8 bar with carbon monoxide, a reaction was carried out for 3 hours at a carbon monoxide flow rate of 500 ml/min and an oxygen flow rate of 35 ml/min. When the reaction product in the reactor was taken out and analyzed by gas chromatography after the end of the reaction, 11.8 g (yield of 22.0%) of diphenyl carbonate (DPC) was obtained. The selectivity of DPC was 98.9%.

EXAMPLE 2

The inside of a reactor containing 47 g (0.50 mol) of phenol, 36.0 mg (0.16 mmol) of palladium acetate (Pd(OAc)$_2$), 136 mg (0.047 mmol) of tungstomolybdenum-phosphoric acid (H$_3$PMo$_6$W$_6$O$_{40}$·30H$_2$O), 28 mg (0.16 mmol) of manganese acetate (Mn(OAc)$_2$), 968 mg (3 mmol) of tetra-n-butylammonium bromide (Bu$_4$NBr) and 7.0 g of a molecular sieve (powder having a particle diameter of 4 Å) was substituted with carbon monoxide. Right after the temperature of the reactor was raised to 80° C. and the pressure of the reactor was increased to 8 bar with carbon monoxide, a reaction was carried out for 9 hours at a carbon monoxide flow rate of 670 ml/min and an oxygen flow rate of 47 ml/min. When the reaction product in the reactor was taken out and analyzed by gas chromatography after the end of the reaction, 20.0 g (yield of 37.3%) of DPC was obtained. The selectivity of DPC was 98.9%.

EXAMPLES 3 to 7

A reaction was carried out for 3 hours by charging 47 g (0.50 mol) of phenol, a heteropoly-acid shown in Table 1, 0.16 mmol of palladium acetate (Pd(OAc)$_2$), 0.69 mmol of benzoquinone, 0.32 mmol of manganese acetate (Mn(OAc)$_2$), 3 mmol of tetra-n-butylammonium bromide (Bu$_4$NBr) and 7.0 g of a molecular sieve (powder having a particle diameter of 4 Å), circulating carbon monoxide at a flow rate of 500 ml/min (standard state) and pure oxygen at a low rate of 35 ml/min (standard state), and maintaining the reaction pressure at 8 bar and the reaction temperature at 80° C. After the end of the reaction, the reaction product in the reactor was taken out and analyzed by gas chromatography. The results are shown in Table 1 together with the used heteropoly-acid.

TABLE 1

| Ex. No. | type of component (c) (heteropoly-acid) (amount mmol) | yield of DPC (%) | selectivity of DPC (%) |
|---|---|---|---|
| Ex. 3 | $H_3PW_6Mo_6O_{40} \cdot 30H_2O$ (0.047) | 21.6 | 98.5 |
| Ex. 4 | $H_3PW_8Mo_4O_{40} \cdot 30H_2O$ (0.046) | 19.6 | 98.1 |
| Ex. 5 | $H_3PW_4Mo_8O_{40} \cdot 30H_2O$ (0.054) | 18.8 | 99.2 |
| Ex. 6 | $H_3PW_{10}Mo_2O_{40} \cdot 30H_2O$ (0.042) | 18.6 | 97.8 |
| Ex. 7 | $H_4SiW_6Mo_6O_{40} \cdot 30H_2O$ (0.047) | 22.0 | 98.0 |

Comparative Example 1

A reaction was carried out for 3 hours by charging 50.0 g (0.53 mol) of phenol, 0.16 mmol of palladium acetate $(Pd(OAc)_2)$, 0.69 mmol of benzoquinone, 0.32 mmol of manganese acetate $(Mn(OAc)_2)$, 3 mmol of tetra-n-butylammonium bromide $(Bu_4NBr)$ and 7.0 g of a molecular sieve (powder having a particle diameter of 4 Å), circulating carbon monoxide at a flow rate of 500 ml/min (standard state) and pure oxygen at a low rate of 30 ml/min (standard state), and maintaining the reaction pressure at 8 bar and the reaction temperature at 80° C. As a result, the amount of formed DPC was 1.09 g (yield of 1.9%) and the selectivity of DPC was about 78%.

EXAMPLE 8

40.0 g (0.43 mol) of phenol, 36.0 mg (0.16 mmol) of palladium acetate $(Pd(OAc)_2)$, 135 mg (0.047 mmol) of tetra-n-butylammonium tungstomolybdenumsilicic acid $((Bu_4N)_4—SiWMo_{11}O_{40})$, 55 mg (0.32 mmol) of manganese acetate $(Mn(OAc)_2)$, 1,000 mg (3.1 mmol) of tetra-n-butylammonium bromide $(Bu_4NBr)$ and 7.0 g of a molecular sieve (powder having a particle diameter of 3 Å) were charged into a reactor and the inside of the reactor was substituted with carbon monoxide. Right after the temperature of the reactor was raised to 80° C. and the pressure of the reactor was increased to 8 bar with carbon monoxide, a reaction was carried out for 3 hours at a carbon monoxide flow rate of 500 ml/min and an oxygen flow rate of 30 ml/min. When the reaction product in the reactor was taken out and analyzed by gas chromatography after the end of there action, 10.6 g (yield of 23.0%) of DPC was obtained. The selectivity of DPC was about 99%.

EXAMPLE 9

40.0 g (0.43 mol) of phenol, 36.0 mg (0.16 mmol) of palladium acetate $(Pd(OAc)_2)$, 145 mg (0.047 mmol) of tetra-n-butylammonium tungstomolybdenumphosphoric acid $((Bu_4N)_3—PW_6MO6O_{40})$, 55 mg (0.32 mmol) of manganese acetate $(Mn(OAc)_2)$, 1,000 mg (3.1 mmol) of tetra-n-butylammonium bromide $(Bu_4NBr)$ and 7.0 g of a molecular sieve (powder having a particle diameter of 3 Å) were charged into a reactor and a reaction was carried out for 3 hours at a carbon monoxide flow rate of 500 ml/min, an oxygen flow rate of 30 ml/min, a reaction pressure of 8 bar and a reaction temperature of 80° C. When the reaction product in the reactor was taken out and analyzed by gas chromatography after the end of the reaction, 10.5 g (yield of 22.8%) of DPC was obtained. The selectivity of DPC was about 99%.

EXAMPLE 10

40.0 g (0.43 mol) of phenol, 36.0 mg (0.16 mmol) of palladium acetate $(Pd(OAc)_2)$, 110 mg (0.047 mmol) of tetraethylammonium molybdenumsilicic acid $((Et_4N)_4—SiMo_{12}O_{40})$, 55 mg (0.32 mmol) of manganese acetate $(Mn(OAc)_2)$, 1,000 mg (3.1 mmol) of tetra-n-butylammonium bromide $(Bu_4NBr)$ and 7.0 g of a molecular sieve (powder having a particle diameter of 3 Å) were charged into a reactor and a reaction was carried out for 3 hours by circulating carbon monoxide at a flow rate of 500 ml/min (standard state) and pure oxygen at a flow rate of 35 ml/min (standard state) and maintaining the reaction pressure at 8 bar and the reaction temperature at 80° C. When the reaction product in the reactor was taken out and analyzed by gas chromatography after the end of the reaction, 9.71 g (yield of 21.1%) of DPC was obtained. The selectivity of DPC was about 98%.

EXAMPLE 11

40.0 g (0.43 mol) of phenol, 36.0 mg (0.16 mmol) of palladium acetate $(Pd(OAc)_2)$, 159 mg (0.047 mmol) of tetrabutylphosphonium tungstomolybdenumsilicic acid $((Bu_4P)_4—SiW_6MO_6O_{40})$, 55 mg (0.32 mmol) of manganese acetate $(Mn(OAc)_2)$, 1,000 mg (3.1 mmol) of tetra-n-butylammonium bromide $(Bu_4NBr)$ and 7.0 g of a molecular sieve (powder having a particle diameter of 3 Å) were charged into a reactor and a reaction was carried out for 3 hours by circulating carbon monoxide at a flow rate of 500 ml/min (standard state) and pure oxygen at a flow rate of 35 ml/min (standard state), and maintaining the reaction pressure at 8 bar and the reaction temperature at 80° C. When the reaction product in the reactor was taken out and analyzed by gas chromatography after the end of the reaction, 10.3 g (yield of 22.4%) of DPC was obtained. The selectivity of DPC was about 97%.

EXAMPLE 12

40.0 g (0.43 mol) of phenol, 36.0 mg (0.16 mmol) of palladium acetate $(Pd(OAc)_2)$, 159 mg (0.047 mmol) of tetra-n-butylammonium tungstomolybdenumsilicic acid $((Bu_4N)_4—SiW_6MO_6O_{40})$, 28 mg (0.16 mmol) of manganese acetate $(Mn(OAc)_2)$, 1,000 mg (3.1 mmol) of tetra-n-butylammonium bromide $(BU_4NBr)$ and 7.0 g of a molecular sieve (powder having a particle diameter of 3 Å) were charged into a reactor and a reaction was carried out for 9 hours by circulating carbon monoxide at a flow rate of 670 ml/min (standard state) and pure oxygen at a flow rate of 47 ml/min (standard state), and maintaining the reaction pressure at 8 bar and the reaction temperature at 80° C. When the reaction product in the reactor was taken out and analyzed by gas chromatography after the end of the reaction, 19.0 g (yield of 41.2%) of DPC was obtained. The selectivity of DPC was 99.4%.

EXAMPLES 13 to 16

0.43 mol of phenol, 0.047 mmol of a quaternary salt of a heteropoly-acid shown in Table 1, 0.16 mmol of palladium acetate (Pd(OAc)$_2$), 0.32 mmol of manganese acetate (Mn(OAc)$_2$), 3.1 mmol of tetra-n-butylammonium bromide (BU$_4$NBr) and 7.0 g of a molecular sieve (powder having a particle diameter of 3 Å) were charged into a reactor and a reaction was carried out for 3 hours by circulating carbon monoxide at a flow rate of 500 ml/min (standard state) and pure oxygen at a flow rate of 35 ml/min (standard state), and maintaining the reaction pressure at 8 bar and the reaction temperature at 80° C. The reaction product in the reactor was taken out and analyzed by gas chromatography after the end of the reaction. The results are shown in Table 2 together with the used heteropoly-acids.

TABLE 2

| Ex. No. | quaternary salt of heteropoly-acid | yield of DPC (%) | selectivity (%) |
| --- | --- | --- | --- |
| Ex. 13 | (Bu$_4$N)$_4$—SiMo$_{12}$O$_{40}$ | 22.7 | 98.6 |
| Ex. 14 | (Bu$_4$N)$_4$—SiW$_6$Mo$_6$O$_{40}$ | 23.0 | 97.4 |
| Ex. 15 | (Bu$_4$N)$_3$—PW$_7$Mo$_5$O$_{40}$ | 20.8 | 98.9 |
| Ex. 16 | (Bu$_4$N)$_3$—HPVMo$_{11}$O$_{40}$ | 17.6 | 98.1 |

EXAMPLE 17

Reparation of Composite of Palladium and Heteropoly-acid 1.15 g (0.5 mmol) of molybdenumsilicic acid (H$_4$SiMo$_{12}$O$_{40}$.nH$_2$O) (of Nippon Inorganic Colour & Chemical Co., Ltd., n≈28) was dissolved in 5 ml of water, and 112 mg of palladium acetate (Pd(OAc)$_2$) was added and heated to evaporate water. At this point, overheating was avoided and a small amount of water was added to repeat heating and evaporation until the added palladium acetate was completely dissolved and a smell of acetic acid disappeared from the evaporated water vapor. Finally, a palladium-heteropoly-acid composite represented by PdH$_2$SiMo$_{12}$O$_{40}$.nH$_2$O was obtained by evaporating water and drying up.

This composite was totally dissolved in 30 ml of water, 20 ml of an aqueous solution containing 0.75 g (2.33 mmol) of tetra-n-butylammonium bromide was added and stirred for about 1 hour, and the formed precipitate was filtered and dried. About 1.57 g of a palladium-heteropoly-acid composite salt which was the tetra-n-butylammonium salt of the above composite represented by (Bu$_4$N)$_2$PdSiMo$_{12}$O$_{40}$.nH$_2$O was obtained as a solid powder.

Reaction Using the Above Palladium-heteropoly-acid Composite 47.0 g (0.5 mol) of phenol, 500 mg (0.16 mmol) of palladium-SiMo$_{12}$O$_{40}$-tetrabutylammonium composite salt ((Bu$_4$N)$_2$PdSiMo$_{12}$O$_{40}$.nH$_2$O), 55 mg (0.32 mmol) of manganese acetate (Mn(OAc)$_2$), 968 mg (3 mmol) of tetra-n-butylammonium bromide (Bu$_4$NBr) and 7.0 g of a molecular sieve (powder having a particle diameter of 4 Å) were charged into a reactor and the inside of the reactor was substituted with carbon monoxide. Right after the temperature of the reactor was raised to 80° C. and the pressure of the reactor was increased to 8 bar with carbon monoxide, a reaction was carried out at a carbon monoxide flow rate of 500 ml/min and an oxygen flow rate of 35 ml/min for 3 hours. When the reaction product in the reactor was taken out and analyzed by gas chromatography after the end of the reaction, 10.3 g (yield of 19.2%) of DPC was obtained. The reaction selectivity was about 98.9%.

EXAMPLE 18

Preparation of Composite of Transition Metal and Heteropoly-acid 1.20 g (0.5 mmol) of tungstomolybdenumsilicic acid (H$_4$SiWMo$_{11}$O$_{40}$.nH$_2$O) (of Nippon Inorganic Colour & Chemical Co., Ltd., n≈27) was dissolved in 5 ml of water, and 168 mg of cerium acetate (Ce(OAc)$_3$) was added and heated to evaporate water. At this point, overheating was avoided and a small amount of water was added to repeat heating and evaporation until the added cerium acetate was completely dissolved and a smell of acetic acid disappeared from the evaporated water vapor. Finally, a cerium-heteropoly-acid composite represented by CeHSiWMo$_{11}$O$_{40}$.nH$_2$O was obtained by evaporating water and drying up.

This composite was totally dissolved in 30 ml of water, 20 ml of an aqueous solution containing 0.24 g (0.75 mmol) of tetra-n-butylammonium bromide was added and stirred for about 1 hour, and the formed precipitate was filtered and dried. About 1.27 g of a cerium-heteropoly-acid composite salt which was a tetra-n-butylammonium salt of the above composite represented by (Bu$_4$N)CeSiWMo$_{11}$O$_{40}$.nH$_2$O was obtained as a solid powder.

Reaction Using the Above Cerium-heteropoly-acid Composite;

50.0 g (0.53 mol) of phenol, 36 mg (0.16 mmol) of palladium acetate (Pd(OAc)$_2$), 96 mg (0.047 mmol) of cerium-tungstomolybdenumsilicic acid composite (CeHSiWMo$_{11}$O$_{40}$.nH$_2$O), 55 mg (0.32 mmol) of manganese acetate (Mn(OAc)$_2$), 968 mg (3 mmol) of tetra-n-butylammonium bromide (Bu$_4$NBr) and 7.0g of a molecular sieve (powder having a particle diameter of 3 Å) were charged into a reactor and the inside of the reactor was substituted with carbon monoxide. Right after the temperature of the reactor was raised to 80° C. and the pressure of the reactor was increased to 8 bar with carbon monoxide, a reaction was carried out for 3 hours at a carbon monoxide flow rate of 500 ml/min and an oxygen flow rate of 35 ml/min. When the reaction product in the reactor was taken out and analyzed by gas chromatography after the end of the reaction, 7.7 g (yield of 13.6%) of DPC was obtained. The selectivity of DPC was 96.7%.

EXAMPLE 19

119 mg (0.047 mmol) of the Cerium-tungstomolybdenumsilicic Acid-tetra-n-butylammonium Composite ((Bu$_4$N)CeSiWMo$_{11}$O$_{40}$.nH$_2$O) prepared in Example 18 was used, 50.0 g (0.53 mol) of phenol, 36 mg (0.16 mmol) of palladium acetate (Pd(OAc)$_2$), 55 mg (0.32 mmol) of manganese acetate (Mn(OAc)$_2$), 967 mg (3.0 mmol) of tetra-n-butylammonium bromide (Bu$_4$NBr) and 7.0 g of a molecular sieve (powder having a particle diameter of 3 Å) were charged into a reactor, and a reaction was carried out for 3 hours at a carbon monoxide flow rate of 500 ml/min, an oxygen flow rate of 30 ml/min, a reaction pressure of 8 bar and a reaction temperature of 80° C. When the reaction product in the reactor was taken out and analyzed by gas chromatography after the end of the reaction, 10.0 g (yield of 17.5%) of DPC was obtained. The selectivity of DPC was 98.1%.

EXAMPLE 20

32.5 g (0.346 mol) of phenol, 10 ml of toluene, and 136 mg (0.047 mmol) of tungstomolybdophosphoric acid ($H_3PMo_6W_6O_{40} \cdot 30H_2O$), 0.16 mmol of palladium acetate ($Pd(OAc)_2$), 0.69 mmol of benzoquinone, 0.32 mmol of manganese acetate ($Mn(OAc)_2$), 3 mmol of tetra-n-butylammonium bromide ($Bu_4NBr$) and 7.0 g of a molecular sieve (powder having a particle diameter of 4 Å) as catalysts were charged into a reactor, and a reaction was carried out for 3 hours by circulating carbon monoxide at a flow rate of 500 ml/min (standard state) and pure oxygen at a flow rate of 35 ml/min (standard state), and maintaining the reaction pressure at 8 bar and the reaction temperature at 80° C. 9.59 g (yield of 25.9%) of DPC was obtained. The selectivity of DPC was 98.9%.

EXAMPLE 21

40.0 g of phenol, 10 g of tetrahydrofuran, 36 mg of palladium acetate ($Pd(OAc)_2$), 55 mg of manganese (II) acetate ($Mn(OAc)_2$), 1,000 mg of tetra-n-butylammonium bromide, 135 mg of tungstomolybdenumsilicic acid tetra-n-butylammonium salt (($Bu_4N)_4SiMo_{11}WO_{40}$) and 7.0 g of a molecular sieve (powder having a particle diameter of 3 Å) were charged into a 100 ml reactor equipped with a gas blowing tube and agitation elements, and the inside of the reactor was substituted with carbon monoxide. Right after the temperature of the reactor was raised to 80° C. and the pressure of the reactor was increased to 8 bar with carbon monoxide, a reaction was carried out for 3 hours by circulating carbon monoxide at a flow rate of 500 ml/min (standard state) and pure oxygen at a flow rate of 35 ml/min (standard state), and maintaining the reaction pressure at 8 bar and the reaction temperature at 80° C. When the reaction product in the reactor was taken out and analyzed by gas chromatography after the end of the reaction, 12.4 g (yield of 27.2%) of DPC was obtained. The selectivity of DPC was 98.8%.

EXAMPLE 22

25.0 g of phenol, 25 g of tetrahydrofuran, 36 mg of palladium acetate ($Pd(OAc)_2$), 55 mg of manganese (II) acetate ($Mn(OAc)_2$), 1,000 mg of tetra-n-butylammonium bromide, 135 mg of tungstomolybdenumsilicic acid tetra-n-butylammonium salt (($Bu_4N)_4SiMO_{11}WO_{40}$) and 7.0 g of a molecular sieve (powder having a particle diameter of 3 Å) were charged into a reactor, and a reaction was carried out in the same manner as in Example 1 for 3 hours by circulating carbon monoxide at a flow rate of 500 ml/min (standard state) and pure oxygen at a flow rate of 35 ml/min (standard state), and maintaining the reaction pressure at 8 bar and the reaction temperature at 80° C. As a result, the amount of formed DPC was 8.89 g (yield of 31.2%) and the selectivity of DPC was 99.5%.

EXAMPLE 23

40.0 g of phenol, 13.0 g of tetrahydrofuran, 36 mg of palladium acetate ($Pd(OAc)_2$), 27.5 mg of manganese (II) acetate ($Mn(OAc)_2$), 1,000 mg of tetra-n-butylammonium bromide, 135 mg of tungstomolybdenumsilicic acid tetra-n-butylammonium salt (($Bu_4N)_4SiMo_{11}WO_{40}$) and 7.0 g of a molecular sieve (powder having a particle diameter of 3 Å) were charged into the same reactor, and a reaction was carried out as in the same manner as in Example 1 for 3 hours by circulating carbon monoxide at a flow rate of 500 ml/min (standard state) and pure oxygen at a flow rate of 35 ml/min (standard state), and maintaining the reaction pressure at 8 bar and the reaction temperature at 80° C. As a result, the amount of formed DPC was 15.5 g (yield of 34.0%) and the selectivity of DPC was 98.8%.

EXAMPLE 24 to 27

A reaction was carried out at 80° C. for 3 hours using 1,2-dimethoxyethane, diethyl ether, 1,4-dioxane or methyl-t-butyl ether in place of tetrahydrofuran. The results are shown in Table 3.

TABLE 3

| Ex. No. | type of ether solvent | yield (%) | selectivity (%) |
| --- | --- | --- | --- |
| Ex. 24 | 1,2-dimethoxyethane | 27.7 | 99.2 |
| Ex. 25 | diethyl ether | 27.6 | 98.3 |
| Ex. 26 | 1,4-dioxane | 23.7 | 98.7 |
| Ex. 27 | methyl-t-butyl ether | 26.6 | 98.6 |

EXAMPLE 28

200 g of phenol, 50 g of tetrahydrofuran, 180 mg of palladium acetate ($Pd(OAc)_2$), 275 mg of manganese (II) acetate ($Mn(OAc)_2$), 5.0 g of tetra-n-butylammonium bromide, 675 mg of tungstomolybdenumsilicic acid tetra-n-butylammonium salt (($Bu_4N)_4SiMo_{11}WO_{40}$) and 35.0 g of a molecular sieve (powder having a particle diameter of 3 Å) were charged into a 500 ml reactor equipped with a gas blowing tube, agitation elements and sample extraction port, and the inside of the reactor was substituted with carbon monoxide. Right after the temperature of the reactor was raised to 80° C. and the pressure of the reactor was increased to 8 bar with carbon monoxide, a reaction was carried out by circulating carbon monoxide at a flow rate of 2.5 l/min (standard state) and pure oxygen at a flow rate of 175 ml/min (standard state) and maintaining the reaction pressure at 8 bar and the reaction temperature at 80° C. As a result, the yield of DPC after 2 hours was 21.9% (selectivity of 99.0%), after 3 hours was 25.0% (selectivity of 98.9%) and after 6 hours was 30.2% (selectivity of 99.1%).

EXAMPLE 29

250 mg (0.08 mmol) of the palladium-heteropoly-acid composite (($Bu_4N)_2PdSiMo_{12}O_{40} \cdot nH_2O$) prepared in Example 17 was used, 20.0 g (0.425 mol) of phenol, 27.5 mg (0.16 mmol) of manganese acetate ($Mn(OAc)_2$), 500 mg (1.5 mmol) of tetra-n-butylammonium bromide ($Bu_4NBr$), 7.0 g of a molecular sieve (powder having a particle diameter of 4 Å) and 30 g of methyl-t-butyl ether as a solvent were charged, and a reaction was carried out for 3 hours by circulating carbon monoxide at a flow rate of 500 ml/min (standard state) and pure oxygen at a flow rate of 35 ml/min (standard state) and maintaining the reaction pressure at 8 bar and the reaction temperature at 80° C. When the reaction product in the reactor was taken out and analyzed by gas chromatography after the end of there action, 6.4 g of DPC (yield of 28.2%) was obtained. The selectivity of DPC was 98.9%.

What is claimed is:

1. A process for producing an aromatic carbonate by reacting an aromatic monohydroxy compound with carbon monoxide and molecular oxygen, wherein
the reaction is carried out under dehydration condition and in the presence of:
(a) palladium or a palladium compound (component (a));
(b) a redox catalyst (component (b));
(c) a heteropoly-acid or salt thereof (component (c)); and
(d) a quaternary ammonium salt or quaternary phosphonium salt (component (d)).

2. The production process of claim 1, wherein the reaction is carried out in the presence of a quinone or hydroquinone.

3. The production process of claim 1, wherein the reaction is carried out under the circulation of carbon monoxide and molecular oxygen.

4. The production process of claim 1, wherein the redox catalyst (component (b)) is a compound of at least one metal selected from the group consisting of manganese, cobalt, copper, cerium and lead.

5. The production process of claim 1, wherein the redox catalyst (component (b)) is a manganese compound or cerium compound.

6. The production process of claim 1, wherein the redox catalyst (component (b)) is a manganese compound.

7. The production process of claim 1, wherein the heteropoly-acid or salt thereof has a Kegin structure and its anion is represented by the following formula (1):

$$X(Mo)_n(W)_m(V)_pO_{40} \qquad (1)$$

wherein X is elemental P, Si or B, and n, m and p are each independently an integer of 0 to 12, with the proviso that n+m+p=12.

8. The production process of claim 1, wherein the reaction is carried out in the presence of a solvent which is inactive in the reaction.

9. The production process of claim 1, wherein the reaction is carried out in the presence of an inert solvent which boils with water.

10. The production process of claim 1, wherein the reaction is carried out in the presence of an organic ether solvent.

11. The production process of claim 1, wherein the component (c) is a quaternary ammonium or quaternary phosphonium salt of a heteropoly-acid.

12. The production process of claim 1, wherein the component (a) and the component (c) form a composite in the catalyst.

13. The production process of claim 1, wherein the reaction is carried out under dehydration conditions (i) in the presence of a molecular sieve, (ii) under the circulation of carbon monoxide and molecular oxygen or (iii) in the presence of a solvent which boils with water.

14. The production process of claim 1, wherein the reaction is carried out at a pressure of 50 kg/cm$^2$G or less.

15. The production process of claim 1, wherein the reaction is carried out under the circulation of a mixed gas of carbon monoxide and molecular oxygen having a molecular oxygen concentration of 10 mol % or less.

* * * * *